United States Patent [19]

Saeva et al.

[11] Patent Number: 4,588,812
[45] Date of Patent: May 13, 1986

[54] SUBSTITUTED 2,3-DIHYDRO-5H-THIAZOLO[2,3,-B]QUINAZOLINE DERIVATIVES

[75] Inventors: Grace A. Saeva; Vassil S. Georgiev, both of Rochester, N.Y.

[73] Assignee: Pennwalt Corporation, Philadelphia, Pa.

[21] Appl. No.: 615,201

[22] Filed: May 30, 1984

[51] Int. Cl.⁴ .................. C07D 513/04; A61K 31/505
[52] U.S. Cl. ..................................... 544/250; 514/885; 544/286
[58] Field of Search .......................... 424/251; 544/250

[56] References Cited

U.S. PATENT DOCUMENTS 2,527,266 10/1950 Kendall et al. ..................... 544/250
4,083,980 4/1978 Schromm et al. .................. 424/251
4,282,360 8/1981 LeMahieu ........................... 544/250
4,486,221 12/1984 Seybold et al. ................. 544/250 X

FOREIGN PATENT DOCUMENTS 0098499 1/1984 European Pat. Off. .

OTHER PUBLICATIONS

Liu, et al., Arch Pharm., 316, pp. 569-571 (06/83).
Liu, et al., Chemical Abstracts, vol. 99, 88155g (1983) (abstract of Liu, et al., Arch Pharm., 316, No. 6, pp. 569-571).
Grosso, et al., J. Med. Chem., vol. 23, No. 11, pp. 1261-1264 (1980).

Primary Examiner—Donald G. Daus
Assistant Examiner—Diana G. Rivers

[57] ABSTRACT

Novel derivatives of 2,3-dihydro-5H-thiazolo[2,3-b]quinazoline, such as (3-oxo-5H-thiazolo[2,3-b]quinazolin-2(3H)-ylidene)acetic acid ethyl ester, N-Benzyl-[3-oxo-5H-thiazolo[2,3-b]quinazolin-2(3H)-ylidene]acetamide, N-tertbutyl-N-benzyl-(3-oxo-5H-thiazolo[2,3-b]quinazolin-2(3H)-ylidene)acetamide, and 2,3-dihydro-3-oxo-5H-thiazolo[2,3-b]quinazoline-2-acetic acid methyl ester; useful as immunomodulators.

14 Claims, No Drawings

SUBSTITUTED 2,3-DIHYDRO-5H-THIAZOLO[2,3,-B]QUINAZOLINE DERIVATIVES

BACKGROUND OF THE INVENTION (1) Field of the Invention

This invention pertains to certain substituted derivatives of 2,3-dihydro-5H-thiazolo[2,3-b]quinazoline.

(2) Description of the Prior Art

The synthesis of derivatives of 2,3-dihydro-5H-thiazolo[2,3-b]quinazoline substituted in the 2 position with —$CH_2$—CO—OH, with —$CH_2$—CO—$NHC_6H_5$, or with =CH—CO—$OCH_3$, and the testing of these derivatives for anti-hypertensive activity, has been reported by Kang-Chien Liu et al, Arch. Pharm. (Weinheim) 316, 569–571 (1983, June issue). The synthesis of 2-(alkylamino)-3,4-dihydro quinazolines, and the extent to which they have anti-hypertensive activity, has been reported by J. A. Grosso et al, *J. Med. Chem.*, 23, 1261–1264 (1980).

BRIEF SUMMARY OF THE INVENTION

This invention relates to compounds of the formula

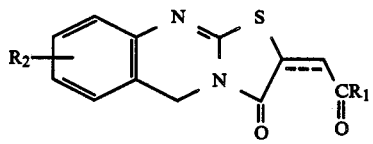

wherein
- $R_1$ is OH, lower($C_1$-$C_4$)alkoxy, $NR_3R_4$, or phenoxy optionally substituted in its phenyl ring with lower($C_1$-$C_4$)alkyl, alkoxy($C_1$-$C_{18}$, branched or unbranched chain) $NO_2$, $NH_2$, lower($C_1$-$C_4$)alkylamino, halogen, OH or trifluoromethyl,
- $R_2$ is H, lower($C_1$-$C_4$)alkyl, alkoxy($C_1$-$C_{18}$, branched or unbranched chain), halogen, trifluoromethyl, $NO_2$ or $NH_2$,
- $R_3$ and $R_4$ are independently H, lower($C_1$-$C_4$)alkyl, $C_3$-$C_7$ cycloalkyl, aryl, allyl, propargyl, 1-adamantanemethyl, benzyl or a $C_4$-$C_6$ heterocyclic ring, or $R_3$ and $R_4$ together with the N adjacent to $R_3$ and $R_4$ form a $C_4$-$C_6$ heterocyclic ring, and
- the exocyclic bond designated by a combination of a dashed line and a straight line in parallel represents either an unsaturated double bond or a saturated bond, provided that, when the exocyclic bond is a saturated bond, $R_1$ is neither phenylamino nor OH.

DETAILED DESCRIPTION

Utility

The compounds of this invention are useful as immunomodulators. Immunomodulatory activity for (3-oxo-5H-thiazolo[2,3-b]quinazolin-2(3H)-ylidene)acetic acid ethyl ester and anti-inflammatory activity has been demonstrated for (3-oxo-5H-thiazolo[2,3-b]quinazolin-2(3H)-ylidene)acetic acid.

Compounds

The compounds of this invention are those of the formula

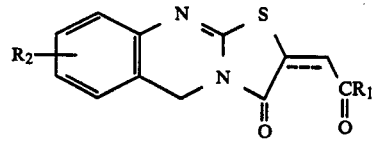

wherein
- $R_1$ is OH, lower($C_1$-$C_4$)alkoxy, $NR_3R_4$, or phenoxy optionally substituted in its phenyl ring with lower($C_1$-$C_4$)alkyl, alkoxy($C_1$-$C_{18}$, branched or unbranched chain), $NO_2$, $NH_2$, lower($C_1$-$C_4$)alkylamino, halogen, OH or trifluoromethyl,
- $R_2$ is H, lower($C_1$-$C_4$)alkyl, alkoxy($C_1$-$C_{18}$, branched or unbranched chain), halogen, trifluoromethyl, $NO_2$ or $NH_2$,
- $R_3$ and $R_4$ are independently H, lower($C_1$-$C_4$)alkyl, $C_3$-$C_7$ cycloalkyl, aryl, allyl, propargyl, 1-adamantanemethyl, benzyl or a $C_4$-$C_6$ heterocyclic ring, or $R_3$ and $R_4$ together with the N adjacent to $R_3$ and $R_4$ form a $C_4$-$C_6$ heterocyclic ring, and
- the exocyclic bond designated by a combination of a dashed line and a straight line in parallel represents either an unsaturated double bond or a saturated bond, provided that, when the exocyclic bond is a saturated bond, $R_1$ is neither phenylamino nor OH.

Formation of the Compounds (1) Preparation of 3,4-dihydro-2(1H)-quinazolinethione optionally substituted in its benzene ring The reaction is summarized as follows:

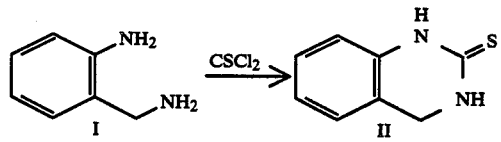

This reaction is performed as described by Grosso et al, *J. Medicinal Chem.*, vol. 23, p. 1261–1264 (1980). Replacement of 2-aminobenzylamine (compound I) by a derivative thereof in which a nuclear hydrogen of the benzene ring is substituted with lower alkyl, alkoxy, halogen, trifluorometnyl, $NO_2$ or $NH_2$, results in the corresponding derivative of 3,4-dihydro-2(1H)-quinazolinethione (compound II).

(2) Preparation of (3-oxo-5H-thiazolo[2,3-b]quinazolin-2(3H)-ylidene)acetic acid and (3-oxo-5H-thiazolo[2,3-b]quinazolin-2(3H)-ylidene)acetic acid lower alkyl esters, optionally substituted in the benzene ring A typical reaction is summarized as follows:

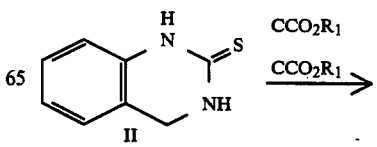

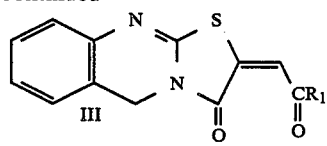

In a typical reaction, the compound, 3,4-dihydro-2(1H)-quinazolinethione (compound II), and an excess of acetylene dicarboxylic acid ($R_1$ is H) are dissolved in toluene and heated at the reflux temperature for about two hours. The reaction mixture is cooled and the (3-oxo-5H-thiazolo[2,3-b]quinazolin-2(3H)-ylidene)acetic acid (compound III, $R_1$ is H), as a precipitate, is first isolated by filtration and then recrystallized from a suitable organic solvent, such as ethyl acetate. Replacement of acetylene dicarboxylic acid by a dialkyl acetylene dicarboxylate in which the alkyl group is lower($C_1$–$C_4$)alkyl, (i.e., $R_1$ is lower alkyl) results in the corresponding (3-oxo-5H-thiazolo[2,3-b]quinazolin-2(3H)-ylidene)acetic acid alkyl ester (compound III, $R_1$ is lower alkyl). Replacement of 3,4-dihydro-2(1H)-quinazolinthione by a derivative thereof in which a nuclear hydrogen of the benzene ring has been substituted with lower alkyl, alkoxy, halogen, trifluoromethyl, $NO_2$, or $NH_2$, group results in the corresponding derivative of either (3-oxo-5H-thiazolo[2,3-b]quinazolin-2(3H)-ylidene)acetic acid or (3-oxo-5H-thiazolo[2,3-b]quinazolin-2(3H)-ylidene)alkyl ester.

(3) Preparation of (3-oxo-5H-thiazolo[2,3-b]quinazolin-2(3H)-ylidene)acetic acid phenyl ester optionally substituted in either the benzene ring or phenyl group; Preparation of (3-oxo-5H-thiazolo[2,3-b]quinazolin-2(3H)-ylidene)acetic acid isopropyl ester A typical reaction is summarized as follows:

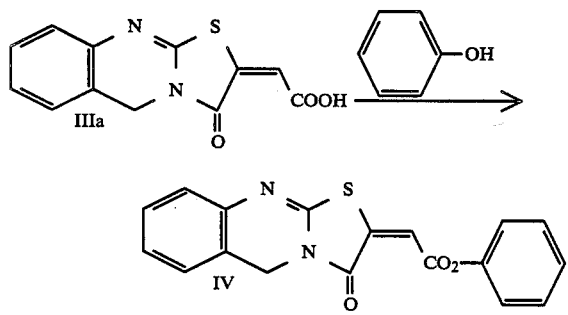

In the typical reaction, the compound, (3-oxo-5H-thiazolo[2,3-b]quinazolin-2(3H)-ylidene)acetic acid (compound IIIa), which can be synthesized as described in the preceding section, phenol, N,N-bis(2-oxo-3-oxazolidinyl) or phosphorodiamidic chloride, and triethylamine are dissolved in dichloromethane, in relative molar amounts of 1, 1.04, 1, and 2, respectively. The reaction mixture is stirred at about 25° C. under nitrogen atmosphere for about 18 hours. An equal volume of water (made slightly basic with sodium bicarbonate) is added. The (3-oxo-5H-thiazolo[2,3-b]quinazolin-2(3H)-ylidene)acetic acid phenyl ester (compound IV), as a precipitate, is isolated by filtration, dried over anhydrous magnesium sulfate, evaporated to dryness under reduced pressure, and then recrystallized from a suitable solvent, such as anhydrous ethanol. Replacement of (3-oxo-5H-thiazolo[2,3-b]quinazolin-2(3H)-ylidene)acetic acid by a derivative thereof in which a nuclear hydrogen of the benzene ring has been substituted with lower alkyl, alkoxy, halogen, trifluoromethyl, $NO_2$, or $NH_2$ and/or replacement of phenol with a derivative thereof in which one of the nuclear hydrogens of its phenyl group has been substituted with a lower alkyl, lower alkoxy, $NO_2$, $NH_2$, lower($C_1$–$C_4$)alkylamino, halogen, OH or trifluoromethyl group results in the formation of the corresponding substituted derivative of (3-oxo-5H-thiazolo[2,3-b]quinazolin-2(3H)-ylidene)acetic acid phenyl ester. Replacement of phenol with isopropanol results in the corresponding (3-oxo-5H-thiazolo[2,3-b]quinazolin-2(3H)-ylidene)acetic acid isopropyl ester.

(4) Preparation of derivatives of (3-oxo-5H-thiazolo[2,3-b]quinazolin-2(3H)-ylidene)acetamide A typical reaction is summarized as follows:

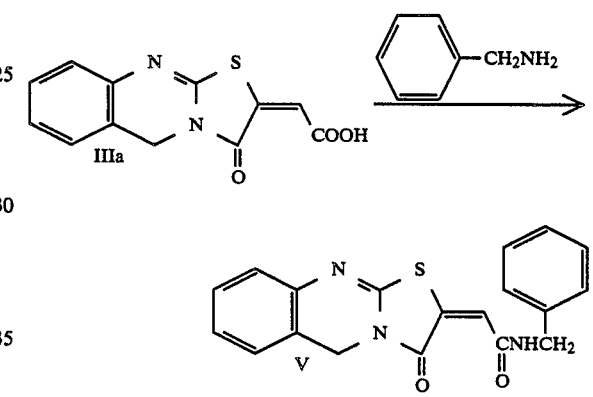

In the typical procedure, the compound, (3-oxo-5H-thiazolo[2,3-b]quinazolin-2(3H)-ylidene)acetic acid (compound IIIa), and benzylamine are dissolved, in relative molar amounts of 1 and 1.1, respectively, in dimethylformamide at 0° C. and the resulting mixture is stirred. To the stirred mixture is added diethylphosphoryl cyanide (in dimethylformamide solution) and triethylamine, in relative molar amounts of 1.1 and 1.1, respectively. The reaction mixture is stirred, for 4 hours at 0° C. and subsequently for about 10 hours at about 25° C. The reaction mixture is diluted with benzene-ethyl acetate and washed sequentially with 5% hydrochloric acid, water, saturated aqueous sodium bicarbonate, and saturated aqueous sodium chloride. The organic phase is dried over anhydrous magnesium sulfate and evaporated under reduced pressure to give N-benzyl-(3-oxo-5H-thiazolo[2,3-b]quinazolin-2(3H)-ylidene)acetamide (compound V). Replacement of benzylamine with p-toluidine, or a primary or secondary amine wherein the nitrogen substituents are selected from lower alkyl, $C_3$–$C_7$ cycloalkyl, aryl (including p-methylphenylamino and p-methoxybenzylamino), allyl, propargyl, 1-adamantanemethyl, or a $C_4$–$C_6$ heterocyclic ring, results in formation of the corresponding mono-substituted or disubstituted derivative of (3-oxo-5H-thiazolo[2,3-b]quinazolin-2(3H)-ylidene)acetamide. Replacement of benzylamine with a secondary amine in which the N of the secondary amine is part of a $C_4$–$C_6$ heterocyclic ring results in formation of the corresponding derivative of (3-oxo-5H-thiazolo[2,3- b]quinazolin-2(3H)-ylidene)acetamide. Replacement of (3-oxo-5H-thiazolo[2,3-b]-2(3H)-ylidene)acetic acid with a derivative thereof in which a nuclear hydrogen of the benzene ring has been substituted with lower alkyl, alkoxy, halogen, trifluoromethyl, NO₂ or NH₂, results in the formation of the corresponding derivative of (3-oxo-5H-thiazolo[2,3-b]quinazolin-2(3H)-ylidene)acetamide.

(5) Formation of N-tert-butyl-N-benzyl(3-oxo-5H-thiazolo[2,3-b]quinazolin-2(3H)-ylidene)acetamide The reaction is summarized as follows:

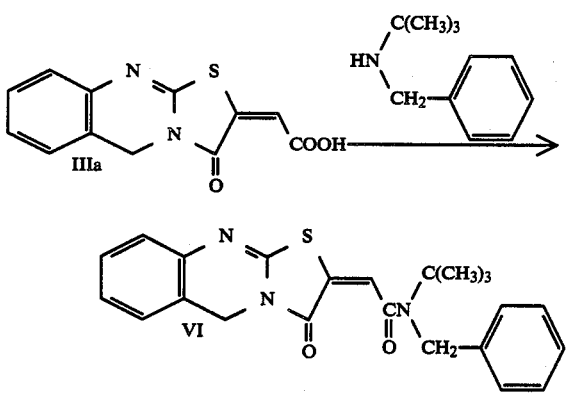

The compound, (3-oxo-5H-thiazolo[2,3-b]quinazolin-2(3H)-ylidene)acetic acid (compound IIIa), triethylamine, and N-(tert-butyl)benzylamine, in relative molar amounts of 1, 2, and 1, respectively, are dissolved in dichloromethane, and the solution is cooled to 10° C. The compound, N,N-bis(2-oxo-3-oxazolidinyl)phosphorodiamidic chloride, (relative molar amount, 1) is added to the reaction mixture, which is then stirred at about 25° C. for about 2 hours. Following acidification with dilute hydrochloric acid, the reaction mixture is filtered, and the organic phase is washed with water, dried over anhydrous magnesium sulfate, and evaporated to dryness under reduced pressure, leaving the N-tert-butyl-N-benzyl(3-oxo-5H-thiazolo[2,3-b]quinazolin-2(3H)-ylidene)acetamide as a solid. The N-tert-butyl-N-benzyl(3-oxo-5H-thiazolo[2,3-b]quinazolin-2(3H)-ylidene)acetamide (compound VI) is then recrystallized from anhydrous ethanol. Replacement of (3-oxo-5H-thiazolo[2,3-b]2(3H)-ylidene)acetic acid with a derivative thereof in which a nuclear hydrogen of the benzene ring has been substituted with lower alkyl, alkoxy, halogen, trifluoromethyl, NO₂ or NH₂, results in the formation of the corresponding derivative of N-tert-butyl-N-benzyl(3-oxo-5H-thiazolo[2,3-b]quinazolin-2(3H)-ylidene)acetamide.

(6) Reduction of the exocyclic double bond at position 2 of the 2.3-dihydro-5-thiazolo[2,3-b]quinazoline moiety The reaction can be summarized as

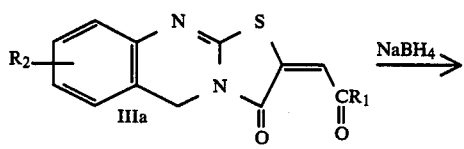

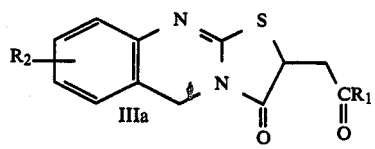

where R₂ and R₁ are defined as above.

A suspension of sodium borohydride (0.08 mol) and tellurium powder (0.034 mol) in 135 ml of anhydrous ethanol is heated under nitrogen atmosphere, preferably for about 15 min. After cooling to −20° C., 8.08 ml glacial acetic acid in 33.65 ml anhydrous ethanol solution (8.08:33.65 v/v) is added dropwise, and the mixture is stirred at −20° C. for 5 min. Stirring is followed by the addition of 0.013 mol of a substituted 2,3-dihydro-5H-thiazol[2,3-b]quinazoline derivative, synthesized by the procedures in the preceding sections (2) to (5), and dissolved in 13.5 ml anhydrous ethanol. The reaction mixture is allowed to warm up to ambient temperature and stirred for about 10 hours. The mixture is filtered through celite, and evaporated under reduced pressure. The residue is taken up in water and extracted with chloroform. The organic extract is dried over anhydrous magnesium sulfate and evaporated under reduced pressure, yielding the corresponding 2,3-dihydro-3-oxo-5H-thiazolo[2,3-b]quinazoline derivative with a saturated exocyclic bond at the 2 position of the 2,3-dihydro-5-thiazo[2,3-b]quinazoline moiety.

ILLUSTRATIVE EXAMPLES

EXAMPLE 1

Preparation of (3-oxo-5H-thiazolo[2,3-b]quinazolin-2(3H)-ylidene) Acid Methyl Ester A solution of 3.34 g (0.02 mol) 3,4-dihydro-2(1H)-quinazolinethione and 3.55 g (0.025 mol) dimethyl acetylenedicarboxylate in 150 ml toluene was refluxed for 2 hours. After cooling, the reaction mixture was filtered and the resulting solid was recrystallized from ethyl acetate, leaving 1.32 g of the title compound as fine yellow crystals. Mp 252°–253° C.

Anal. Calcd for $C_{13}H_{10}N_2O_3S$: C, 56.93; H, 3.67; N, 10.21; S, 11.69: Found: C, 56.95; H, 3.74; N, 10.14; S, 11.69.

EXAMPLE 2

Preparation of (3-oxo-5H-thiazolo[2,3-b]quinazolin-2(3H)-ylidene)acetic Acid Ethyl Ester The compound, (3-oxo-5H-thiazolo[2,3-b]quinazolin-2(3H)-ylidene)acetic acid ethyl ester, was synthesized by following the procedure in Example 1, except that diethyl acetylenedicarboxylate was used instead of dimethyl acetylenedicarboxylate. Mp 222°–224° C.

Anal. Calcd for $C_{14}H_{12}N_2O_3S$: C, 58.32; H, 4.19; N, 9.72; S, 11.12. Found: C, 58.36; H, 4.29; N, 9.70; S, 11.20.

The compound had immunomodulatory activity in the Kennedy Plaque Assay, (J. C. Kennedy et al, Immunol., vol. 20, p. 253 (1971), when administered to the animals either three times p.o. at a dose of 3.125 mg/kg body weight or three times i.p. at a dose of 6.25 mg/kg body weight.

EXAMPLE 3

Preparation of (3-oxo-5H-thiazolo[2,3-b]quinazolin-2(3H)-ylidene)acetic Acid

The compound, (3-oxo-5H-thiazolo[2,3-b]quinazolin-2(3H)-ylidene)acetic acid was synthesized by following the procedure in example 1, except that acetylene dicarboxylic acid was used instead of dimethyl acetylene dicarboxylate and the compound was recrystallized from isopropanol instead of ethyl acetate. Mp 263°–264° C.

Anal. Calcd for $C_{12}H_8N_2O_3S$: C, 55.38; H, 3.10; N, 10.76; S, 12.32. Found: C, 55.21; H, 3.36; N, 10.64; S, 12.56.

The compound, when administered to rats, inhibited carageenan-induced paw edema.

EXAMPLE 4

Preparation of (3-oxo-5H-thiazolo[2,3-b]quinazolin-2(3H)-ylidene)acetic Acid Phenyl Ester A solution of 1.30 g (5 mmols) (3-oxo-5H-thiazolo[2,3-b]quinazolin-2(3H)-ylidene)acetic acid, 1.27 g (5 mmols) N,N-bis(2-oxo-3-oxazolidinyl)phosphorodiamidic chloride, 0.49 g (5.2 mmols) phenol, and 1.10 g (10 mmols) triethylamine, in 10 ml dichloromethane was stirred at room temperature, under nitrogen atmosphere for 18 hours. Then, 10 ml of water (made slightly basic with sodium bicarbonate) were added. The precipitate was filtered of and the filtrate was dried over anhydrous magnesium sulfate, and evaporated to dryness under reduced pressure. The residual orange-yellow solid was recrystallized from anhydrous ethanol. Yield—0.62 g. Mp 194°–195° C.

Anal. Calcd for $C_{18}H_{12}N_2O_3S$: C, 64.27; H, 3.60; N, 8.33; S, 9.53. Found: C, 64.48; H, 3.64; N, 8.38; S, 9.96.

EXAMPLE 5

Preparation of N-Benzyl-(3-oxo-5H-thiazolo[2,3-b]quinazolin-2(3H)-ylidene)acetamide To a stirred mixture of (3-oxo-5H-thiazolo[2,3-b]quinazolin-2(3H)-ylidene)acetic acid (10.5 g, 1.9 mmols) and benzylamine (0.23 g, 2.1 mmols) in 25 ml dimethylformamide at 0° C., was added diethylphosphoryl cyanide (0.28 g, 2.1 mmols) (in dimethylformamide solution), followed by triethylamine (0.41 g, 4.0 mmols). The reaction mixture was stirred for 4 hours at 0° C. and then, at room temperature overnight. The reaction mixture was diluted with benzene-ethyl acetate and washed sequentially with 5% hydrochloric acid, water, saturated aqueous sodium bicarbonate and saturated aqueous sodium chloride. The organic solution was dried over anhydrous magnesium sulfate, and evaporated to dryness under reduced pressure to give N-Benzyl-(3-oxo-5H-thiazolo[2,3-b]quinazolin-2(3H)-ylidene)acetamide which was recrystallized from ethyl acetate. Yield—0.09 g. Mp 258°–259° C.

Anal. Calcd for $C_{19}H_{15}N_3O_2S$: C, 65.31; H, 4.33; N, 12.03; S, 9.18. Found: C, 64.94; H, 4.48; N, 11.85; S, 9.15.

EXAMPLE 6

Preparation of N-Cyclohexyl-(3-oxo-5H-thiazolo[2,3-b]quinazolin-2(3H)-ylidene)acetamide The compound, N-Cyclohexyl-(3-oxo-5H-thiazolo[2,3-b]quinazolin-2(3H)-ylidene)acetamide, was synthesized by the procedure in Example 5, except that cyclohexylamine was used instead of benzylamine and the compound was recrystallized from anhydrous ethanol instead of ethyl acetate. Mp 287°–288° C.

Anal. Calcd for $C_{18}H_{19}N_3O_2S$: C, 63.32; H, 5.61; N, 12.31; S, 9.39. Found: C, 63.16; H, 5.59; N, 12.25; S, 9.48.

EXAMPLE 7

Preparation of N-Allyl-(3-oxo-5H-thiazolo[2,3-b]quinazolin-2(3H)-ylidene)acetamide The compound, N-allyl-(3-oxo-5H-thiazolo[2,3-b]quinazolin-2(3H)-ylidene)acetamide was made by the procedure in Example 5, except that allylamine was used instead of benzylamine and the compound was recrystallized from anhydrous ethanol instead of ethyl acetate. Mp 275°–276° C.

Anal. Calcd for $C_{15}H_{13}N_3O_2S$: C, 60.19; H, 4.38; N, 14.04; S, 10.71. Found: C, 59.93; H, 4.45; N, 13.94; S, 10.50.

EXAMPLE 8

Preparation of N-(1-Adamantanemethyl)-(3-oxo-5H-thiazolo[2,3-b]quinazolin-2(3H)-ylidene)acetamide The compound, N-(1-adamantanemethyl)-(3-oxo-5H-thiazolo[2,3-b]quinazolin-2(3H)-ylidene)acetamide was synthesized by the procedure in Example 5 except that (1-adamantanemethyl)amine was used instead of benzylamine and the compound was recrystallized from chloroform instead of ethyl acetate. Mp 294°–295° C.

Anal. Calcd for $C_{23}H_{25}N_3O_2S$: C, 67.79; H, 6.18; N, 10.31; S, 7.87. Found: C, 67.16; H, 6.13; N, 10.21; S, 7.81.

EXAMPLE 9

Preparation of N-tert-Butyl-N-benzyl-(3-oxo-5H-thiazolo[2,3-b]quinazolin-2(3H)-ylidene)acetamide A solution of (3-oxo-5H-thiazolo[2,3-b]quinazolin-2(3H)-ylidene)acetic acid (1.3 g, 5 mmols), triethylamine (1.5 ml, 0.01 mol), and N-(tert-butyl)benzylamine (0.93 ml, 5 mmols) in 10 ml dichloromethane, was cooled to 10° C. Then, 1.27 g (5 mmols) of N,N-bis(2-oxo-3-oxazolidinyl)phosphorodiamidic chloride was added, and the reaction mixture was stirred at room temperature for 20 hours. Following acidification with dilute hydrochloric acid, the reaction mixture was filtered and the organic layer was washed with water, dried over anhydrous magnesium sulfate, and evaporated to dryness under reduced pressure leaving an orange-yellow solid which was recrystallized from anhydrous ethanol. Yield—0.71 g. Mp 195°–197° C.

Anal. Calcd for $C_{25}H_{23}N_3O_2S$: C, 68.12; H, 5.72; N, 10.36; S, 7.91. Found: C, 67.85; H, 5.79; N, 10.34; S, 8.04.

EXAMPLE 10

Preparation of 2,3-Dihydro-3-oxo-5H-thiazolo[2,3-b]quinazoline-2-acetic Acid Methyl Ester A suspension of sodium borohydride (3.03 g, 0.08 mol) and 4.38 g (0.034 mol) tellurium powder in 135 ml anhydrous ethanol was heated under nitrogen atmosphere for 15 min. After cooling to −20° C., 8.08 ml glacial acetic acid in 33.65 ml anhydrous ethanol was added dropwise, and the mixture was stirred at that temperature for 5 min, followed by the addition of 3.50 g (0.013 mol) of (3-oxo-5H-thiazolo[2,3-b]quinazolin-2(3H)-ylidene)acetic acid methyl ester in 13.5 ml anhydrous ethanol. The reaction mixture was allowed to warm up to ambient temperature and stirred overnight. Then, the mixture was filtered through celite, and evaporated under reduced pressure. The residue was taken up in water and extracted with chloroform. The organic extract was dried over anhydrous magnesium sulfate and evaporated under reduced pressure, yielding 1.16 g of 2,3-dihydro-3-oxo-5H-thiazolo[2,3-b]quinazoline-2-acetic acid methyl ester. Mp 143°–144° C. after recrystallization from ethyl acetate.

Anal. Calcd for $C_{13}H_{12}N_2O_3S$: C, 56.51; H, 4.38; N, 10.14; S, 11.60. Found: C, 56.16; H, 4.43; N, 10.17; S, 11.50.

EXAMPLE 11

Preparation of 2,3-dihydro-3-oxo-5H-thiazolo[2,3-b]quinazoline-2-acetic acid ethyl ester The compound, 2,3-dihydro-3-oxo-5H-thiazolo[2,3-b]quinazoline-2-acetic acid ethyl ester, was synthesized by the procedure in Example 10 except that (3-oxo-5H-thiazolo[2,3-b]quinazolin-2(3H)-ylidene)acetic acid methyl ester was used instead of the corresponding methyl ester and the compound was recrystallized from ether instead of ethyl acetate. Mp 130°–142° C.

Anal. Calcd for $C_{14}H_{14}N_2O_3S$: C, 57.92; H, 4.86; N, 9.65; S, 11.04. Found: C, 57.73; H, 4.96; N, 9.58; S, 10.80.

What is claimed is:

1. A compound of the formula

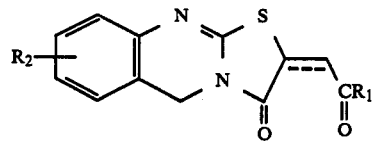

wherein
$R_1$ is OH, $C_1$–$C_4$ alkoxy, $NR_3R_4$, or phenoxy optionally substituted in its phenyl ring with $C_1$–$C_4$ alkyl, alkoxy($C_1$–$C_{18}$, branched or unbranched chain), $NO_2$, $NH_2$, $C_1$–$C_4$ alkylamino, halogen, OH, or trifluoromethyl,
$R_2$ is H, $C_1$–$C_4$ alkyl, alkoxy($C_1$–$C_{18}$, branched or unbranched chain), halogen, trifluoromethyl, $NO_2$, or $NH_2$,
$R_3$ and $R_4$ are independently H, $C_1$–$C_4$ alkyl, $C_3$–$C_7$ cycloalkyl, phenyl, allyl, propargyl, 1-adamantanemethyl, benzyl, or $R_3$ and $R_4$ together with the N adjacent to $R_3$ and $R_4$ form a $C_4$–$C_6$ heterocyclic ring, and
the exocyclic bond designated by a combination of a dashed line and a straight line in parallel represents either an unsaturated double bond or a saturated bond, provided that, when the exocyclic bond is a saturated bond, $R_1$ is neither phenylamino nor OH.

2. The compound as defined in claim 1 wherein the exocyclic bond designated by a combination of a dashed line and a straight line in parallel represents an unsaturated double bond.

3. The compound as defined in claim 2 wherein $R_1$ is methoxy and $R_2$ is H.

4. The compound as defined in claim 2 wherein $R_1$ is ethoxy and $R_2$ is H.

5. The compound as defined in claim 1 wherein $R_1$ is phenoxy.

6. The compound as defined in claim 2 wherein $R_1$ is $NR_3R_4$, $R_2$ is H, $R_3$ is H and $R_4$ is benzyl.

7. The compound as defined in claim 2 wherein $R_1$ is $NR_3R_4$, $R_2$ is H, $R_3$ is H, and $R_4$ is cyclohexyl.

8. The compound as defined in claim 2 wherein $R_1$ is $NR_3R_4$, $R_2$ is H, $R_3$ is H and $R_4$ is allyl.

9. The compound as defined in claim 2 wherein $R_1$ is $NR_3R_4$, $R_2$ is H, $R_3$ is H and $R_4$ is 1-adamantanemethyl.

10. The compound as defined in claim 2 wherein $R_1$ is $NR_3R_4$, $R_2$ is H, $R_3$ is benzyl and $R_4$ is tertiary butyl.

11. The compound as defined in claim 1 wherein the exocyclic bond designated by a combination of a dashed line and a straight line in parallel represents a saturated bond.

12. The compound as defined in claim 11 wherein $R_1$ is methoxy and $R_2$ is H.

13. The compound as defined in claim 11 wherein $R_1$ is ethoxy and $R_2$ is H.

14. The compound as defined in claim 2 wherein $R_1$ is OH and $R_2$ is H.

* * * * *